United States Patent
Blair

(10) Patent No.: US 9,763,742 B2
(45) Date of Patent: Sep. 19, 2017

(54) WIRELESSLY DETECTABLE OBJECTS FOR USE IN MEDICAL PROCEDURES AND METHODS OF MAKING SAME

(71) Applicant: RF Surgical Systems, Inc., Carlsbad, CA (US)

(72) Inventor: William A. Blair, Carlsbad, CA (US)

(73) Assignee: Covidien LP, Mansfield, MA (US)

(*) Notice: Subject to any disclaimer, the term of this patent is extended or adjusted under 35 U.S.C. 154(b) by 313 days.

(21) Appl. No.: 14/247,960

(22) Filed: Apr. 8, 2014

(65) Prior Publication Data

US 2014/0303580 A1    Oct. 9, 2014

Related U.S. Application Data

(63) Continuation of application No. 12/606,686, filed on Oct. 27, 2009, now Pat. No. 8,726,911.

(Continued)

(51) Int. Cl.
| | |
|---|---|
| *A61B 19/00* | (2006.01) |
| *A61F 13/00* | (2006.01) |
| *G06K 19/04* | (2006.01) |
| *A61B 90/90* | (2016.01) |
| *A61B 90/98* | (2016.01) |
| *A61B 90/00* | (2016.01) |

(52) U.S. Cl.
CPC ............. *A61B 19/44* (2013.01); *A61B 90/39* (2016.02); *A61B 90/90* (2016.02); *A61B 90/98* (2016.02); *A61F 13/00051* (2013.01); *G06K 19/04* (2013.01); *A61B 2090/3966* (2016.02); *Y10T 29/49016* (2015.01); *Y10T 29/49817* (2015.01)

(58) Field of Classification Search
CPC ............... G06K 19/04; A61F 13/00051; Y10T 29/49817; Y10T 29/49016; A61B 19/44; A61B 90/90; A61B 90/39; A61B 2090/3966; A61B 90/98
See application file for complete search history.

(56) References Cited

U.S. PATENT DOCUMENTS

| | | |
|---|---|---|
| 2,740,405 A | 4/1956 | Riordan |
| 3,031,864 A | 5/1962 | Freundlich |

(Continued)

FOREIGN PATENT DOCUMENTS

| | | |
|---|---|---|
| AU | 199852698 B2 | 3/1993 |
| AU | 2003249257 A1 | 2/2004 |

(Continued)

OTHER PUBLICATIONS

Macario et al., "Initial Clinical Evaluation of a Handheld Device for Detecting Retained Surgical Gauze Sponges Using Radiofrequency Identification Technology," Arch Surg 141:659-662, Jul. 2006.

(Continued)

*Primary Examiner* — Christine H Matthews
*Assistant Examiner* — Joshua D Lannu

(57) ABSTRACT

Various embodiments of a wirelessly detectable object to be used in medical procedures are provided. The object may include a piece of absorbent material, a transponder to wirelessly receive and transmit signals, and a cover. The cover is attached directly to the piece of absorbent material to retain the transponder. Methods of manufacturing wirelessly detectable objects are also provided.

7 Claims, 14 Drawing Sheets

Related U.S. Application Data

(60) Provisional application No. 61/109,142, filed on Oct. 28, 2008.

(56) References Cited

U.S. PATENT DOCUMENTS

| | | | |
|---|---|---|---|
| 3,422,816 A | 1/1969 | Robinson et al. |
| 3,587,583 A | 6/1971 | Greenberg |
| D240,166 S | 6/1976 | Testa |
| 4,034,297 A | 7/1977 | Giorgi et al. |
| 4,114,601 A | 9/1978 | Abels |
| 4,193,405 A | 3/1980 | Abels |
| D272,943 S | 3/1984 | Cartmell et al. |
| 4,477,256 A | 10/1984 | Hirsch |
| 4,540,398 A | 9/1985 | Barson et al. |
| 4,603,074 A * | 7/1986 | Pate | D06N 3/06 427/331 |
| 4,626,251 A | 12/1986 | Shen |
| 4,636,208 A | 1/1987 | Rath |
| 4,639,253 A | 1/1987 | Dyer et al. |
| 4,645,499 A | 2/1987 | Rupinskas |
| 4,658,818 A | 4/1987 | Miller, Jr. et al. |
| 4,681,111 A | 7/1987 | Silvian |
| 4,704,109 A | 11/1987 | Rupinskas |
| 4,718,897 A | 1/1988 | Elves |
| 4,893,118 A | 1/1990 | Lewiner et al. |
| 4,917,694 A | 4/1990 | Jessup |
| 4,935,019 A | 6/1990 | Papp, Jr. |
| 4,938,901 A | 7/1990 | Groitzsch et al. |
| 4,966,595 A | 10/1990 | Meringola |
| 4,992,675 A | 2/1991 | Conner, Jr. et al. |
| 5,041,103 A | 8/1991 | Rupinskas |
| 5,045,080 A | 9/1991 | Dyer et al. |
| 5,049,219 A | 9/1991 | Johns et al. |
| 5,057,095 A | 10/1991 | Fabian |
| 5,090,410 A | 2/1992 | Saper et al. |
| 5,105,829 A | 4/1992 | Fabian et al. |
| 5,107,862 A | 4/1992 | Fabian et al. |
| 5,112,325 A | 5/1992 | Zachry |
| D330,872 S | 11/1992 | Ball |
| 5,181,021 A | 1/1993 | Lee et al. |
| 5,188,126 A | 2/1993 | Fabian et al. |
| 5,190,059 A | 3/1993 | Fabian et al. |
| 5,203,767 A | 4/1993 | Cloyd |
| 5,224,593 A | 7/1993 | Bennett |
| 5,231,273 A | 7/1993 | Caswell et al. |
| 5,235,326 A | 8/1993 | Beigel et al. |
| 5,241,923 A | 9/1993 | Janning |
| 5,329,944 A | 7/1994 | Fabian et al. |
| 5,353,011 A | 10/1994 | Wheeler et al. |
| D353,343 S | 12/1994 | Eberhardt |
| D354,927 S | 1/1995 | Andrau |
| D356,052 S | 3/1995 | Andrau |
| D359,705 S | 6/1995 | Ball |
| 5,446,447 A | 8/1995 | Carney et al. |
| 5,456,718 A | 10/1995 | Szymaitis |
| 5,575,781 A | 11/1996 | DeBusk |
| D378,614 S | 3/1997 | Jensen |
| 5,650,596 A | 7/1997 | Morris et al. |
| 5,664,582 A | 9/1997 | Szymaitis |
| D385,037 S | 10/1997 | Jensen |
| 5,725,517 A | 3/1998 | DeBusk |
| 5,767,816 A | 6/1998 | Cosman |
| 5,792,128 A | 8/1998 | DeBusk |
| D412,135 S | 7/1999 | Saito |
| 5,923,001 A | 7/1999 | Morris et al. |
| 5,931,824 A | 8/1999 | Stewart et al. |
| 5,963,132 A | 10/1999 | Yoakum |
| 5,969,613 A | 10/1999 | Yeager et al. |
| D418,773 S | 1/2000 | Saito |
| 6,026,818 A | 2/2000 | Blair et al. |
| D423,673 S | 4/2000 | Bassøe |
| 6,093,869 A | 7/2000 | Roe et al. |
| D429,337 S | 8/2000 | Sanfilippo |
| 6,172,608 B1 | 1/2001 | Cole |
| 6,201,469 B1 | 3/2001 | Balch et al. |
| 6,211,666 B1 | 4/2001 | Acker |
| 6,232,878 B1 | 5/2001 | Rubin |
| 6,276,033 B1 | 8/2001 | Johnson et al. |
| 6,317,027 B1 | 11/2001 | Watkins |
| 6,349,234 B2 | 2/2002 | Pauly et al. |
| 6,353,406 B1 | 3/2002 | Lanzl et al. |
| 6,354,493 B1 | 3/2002 | Mon |
| 6,359,562 B2 | 3/2002 | Rubin |
| 6,366,206 B1 | 4/2002 | Ishikawa et al. |
| D456,907 S | 5/2002 | Sanfilippo |
| D457,634 S | 5/2002 | Rouns et al. |
| 6,384,296 B1 | 5/2002 | Roe et al. |
| 6,401,722 B1 | 6/2002 | Krag |
| 6,441,741 B1 | 8/2002 | Yoakum |
| D471,281 S | 3/2003 | Baura et al. |
| 6,557,752 B1 | 5/2003 | Yacoob |
| 6,566,997 B1 | 5/2003 | Bradin |
| 6,588,661 B2 | 7/2003 | Degrauwe et al. |
| 6,632,216 B2 | 10/2003 | Houzego et al. |
| 6,633,226 B1 | 10/2003 | Nysen |
| 6,641,039 B2 | 11/2003 | Southard |
| 6,648,223 B2 | 11/2003 | Boukhny et al. |
| 6,650,143 B1 | 11/2003 | Peng |
| 6,650,240 B2 | 11/2003 | Lee et al. |
| 6,654,629 B2 | 11/2003 | Montegrande |
| 6,667,902 B2 | 12/2003 | Peng |
| 6,671,040 B2 | 12/2003 | Fong et al. |
| 6,696,954 B2 | 2/2004 | Chung |
| 6,700,151 B2 | 3/2004 | Peng |
| 6,734,795 B2 | 5/2004 | Price |
| 6,747,561 B1 | 6/2004 | Reeves |
| 6,749,554 B1 | 6/2004 | Snow et al. |
| 6,753,783 B2 | 6/2004 | Friedman et al. |
| 6,766,960 B2 | 7/2004 | Peng |
| D495,055 S | 8/2004 | Silber |
| 6,774,800 B2 | 8/2004 | Friedman et al. |
| 6,777,623 B2 | 8/2004 | Ballard |
| 6,777,757 B2 | 8/2004 | Peng et al. |
| 6,778,089 B2 | 8/2004 | Yoakum |
| 6,786,405 B2 | 9/2004 | Wiedenhoefer |
| 6,791,891 B1 | 9/2004 | Peng et al. |
| 6,798,693 B2 | 9/2004 | Peng |
| 6,812,824 B1 | 11/2004 | Goldinger et al. |
| 6,812,842 B2 | 11/2004 | Dimmer |
| 6,822,570 B2 | 11/2004 | Dimmer et al. |
| 6,822,888 B2 | 11/2004 | Peng |
| 6,838,990 B2 | 1/2005 | Dimmer |
| 6,856,540 B2 | 2/2005 | Peng et al. |
| D502,419 S | 3/2005 | Copen |
| 6,861,639 B2 | 3/2005 | Al-Ali |
| 6,861,954 B2 | 3/2005 | Levin |
| 6,875,199 B2 | 4/2005 | Altman |
| 6,879,300 B2 | 4/2005 | Rochelle et al. |
| 6,898,116 B2 | 5/2005 | Peng |
| 6,909,366 B1 | 6/2005 | Marsh et al. |
| 6,940,751 B2 | 9/2005 | Peng et al. |
| D511,004 S | 10/2005 | Masuda |
| 6,956,258 B2 | 10/2005 | Peng |
| D511,384 S | 11/2005 | Masuda |
| 6,972,986 B2 | 12/2005 | Peng et al. |
| 6,977,504 B2 | 12/2005 | Wright et al. |
| 6,982,646 B2 | 1/2006 | Rodgers et al. |
| 6,992,925 B2 | 1/2006 | Peng |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,026,927 B2 | 4/2006 | Wright et al. |
| 7,031,209 B2 | 4/2006 | Wang et al. |
| 7,037,336 B2 | 5/2006 | Ward |
| 7,042,722 B2 | 5/2006 | Suzuki et al. |
| D526,586 S | 8/2006 | McCaghren et al. |
| 7,088,248 B2 | 8/2006 | Forster |
| 7,098,793 B2 | 8/2006 | Chung |
| 7,118,029 B2 * | 10/2006 | Nycz | A61B 90/98 235/375 |
| 7,135,973 B2 | 11/2006 | Kittel et al. |
| 7,135,978 B2 | 11/2006 | Gisselberg et al. |

(56) References Cited

U.S. PATENT DOCUMENTS

| | | |
|---|---|---|
| 7,142,118 B2 | 11/2006 | Hamilton et al. |
| 7,142,815 B2 | 11/2006 | Desjeux et al. |
| D534,448 S | 1/2007 | Shaffer, II et al. |
| 7,158,030 B2 | 1/2007 | Chung |
| 7,158,754 B2 | 1/2007 | Anderson |
| 7,160,258 B2 | 1/2007 | Imran et al. |
| D536,673 S | 2/2007 | Silber |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,227,469 B2 | 6/2007 | Varner et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,269,047 B1 | 9/2007 | Fong et al. |
| 7,299,981 B2 | 11/2007 | Hickle et al. |
| D557,423 S | 12/2007 | Chen |
| D558,352 S | 12/2007 | Sanfilippo |
| 7,304,911 B2 | 12/2007 | Davies et al. |
| 7,307,530 B2 | 12/2007 | Fabian et al. |
| D558,882 S | 1/2008 | Brady |
| 7,319,396 B2 | 1/2008 | Homanfar et al. |
| 7,319,397 B2 | 1/2008 | Chung et al. |
| 7,325,723 B2 | 2/2008 | Desjeux |
| 7,333,013 B2 | 2/2008 | Berger |
| 7,342,497 B2 | 3/2008 | Chung et al. |
| 7,362,228 B2 | 4/2008 | Nycz et al. |
| D568,186 S | 5/2008 | Blair et al. |
| 7,382,255 B2 | 6/2008 | Chung |
| 7,397,364 B2 | 7/2008 | Govari |
| 7,399,899 B2 | 7/2008 | Fabian |
| 7,420,468 B2 | 9/2008 | Fabian et al. |
| 7,423,535 B2 | 9/2008 | Chung et al. |
| 7,446,646 B2 | 11/2008 | Huomo |
| 7,449,614 B2 | 11/2008 | Ales, III |
| 7,464,713 B2 | 12/2008 | Fabian et al. |
| 7,465,847 B2 | 12/2008 | Fabian |
| 7,471,541 B2 | 12/2008 | Fong et al. |
| D584,414 S | 1/2009 | Lash et al. |
| 7,474,222 B2 | 1/2009 | Yang et al. |
| 7,492,257 B2 | 2/2009 | Tethrake et al. |
| 7,492,261 B2 | 2/2009 | Cambre et al. |
| 7,492,263 B2 | 2/2009 | Marsilio et al. |
| 7,508,308 B2 | 3/2009 | Chung |
| 7,511,604 B2 | 3/2009 | Raphaeli et al. |
| D590,342 S | 4/2009 | Dávila et al. |
| 7,513,425 B2 | 4/2009 | Chung |
| 7,541,933 B2 | 6/2009 | Volpi et al. |
| 7,557,710 B2 | 7/2009 | Sanchez et al. |
| D598,110 S | 8/2009 | Phillips et al. |
| D598,114 S | 8/2009 | Cryan |
| 7,579,951 B2 | 8/2009 | Hirahara et al. |
| 7,590,441 B2 | 9/2009 | Govari et al. |
| 7,596,850 B2 | 10/2009 | Barth et al. |
| 7,609,538 B1 | 10/2009 | Lee et al. |
| 7,644,016 B2 | 1/2010 | Nycz et al. |
| 7,696,877 B2 | 4/2010 | Barnes et al. |
| 7,703,674 B2 | 4/2010 | Stewart et al. |
| 7,721,935 B2 | 5/2010 | Racenet et al. |
| 7,769,422 B2 | 8/2010 | DiSilvestro et al. |
| 7,778,687 B2 | 8/2010 | Dimmer et al. |
| 7,780,613 B2 | 8/2010 | Sherman |
| 7,787,931 B2 | 8/2010 | Fabian et al. |
| 7,795,491 B2 | 9/2010 | Stewart et al. |
| 7,837,694 B2 | 11/2010 | Tethrake et al. |
| 7,855,656 B2 | 12/2010 | Maschke |
| 7,876,097 B2 | 1/2011 | Greim |
| 7,898,420 B2 | 3/2011 | Blair et al. |
| 8,082,192 B2 | 12/2011 | Nycz et al. |
| 8,105,296 B2 | 1/2012 | Morris et al. |
| 8,111,162 B2 | 2/2012 | Barnes et al. |
| 8,181,860 B2 | 5/2012 | Fleck et al. |
| 8,186,587 B2 | 5/2012 | Zmood et al. |
| 8,193,938 B2 | 6/2012 | Halberthal et al. |
| 8,196,589 B2 | 6/2012 | Gisselberg et al. |
| 8,259,518 B2 | 9/2012 | Peng et al. |
| 8,279,068 B2 | 10/2012 | Morris et al. |
| 8,371,448 B1 | 2/2013 | Reaux |
| 8,454,613 B2 | 6/2013 | Tethrake et al. |
| 8,477,076 B1 | 7/2013 | Nero, Jr. et al. |
| 8,576,076 B2 | 11/2013 | Morris et al. |
| 8,780,660 B2 | 7/2014 | Peng |
| 8,872,662 B2 | 10/2014 | Halberthal et al. |
| 8,978,229 B2 | 3/2015 | Halberthal et al. |
| 8,985,446 B2 | 3/2015 | Fleck et al. |
| 8,994,358 B2 | 3/2015 | McElhinny et al. |
| 9,041,479 B2 | 5/2015 | Nero, Jr. et al. |
| 9,119,667 B2 | 9/2015 | Halberthal et al. |
| 9,168,104 B2 | 10/2015 | Dein |
| 9,414,973 B2 | 8/2016 | Fleck et al. |
| 2002/0032435 A1 | 3/2002 | Levin |
| 2002/0070863 A1 | 6/2002 | Brooking |
| 2003/0219566 A1* | 11/2003 | Berkowitz ............ A47G 9/062 428/100 |
| 2004/0250819 A1 | 12/2004 | Blair et al. |
| 2005/0203470 A1 | 9/2005 | Ballard |
| 2005/0247794 A1 | 11/2005 | Jones et al. |
| 2005/0267550 A1 | 12/2005 | Hess et al. |
| 2006/0047238 A1 | 3/2006 | Galdenzi et al. |
| 2006/0054107 A1* | 3/2006 | Baker ................ A01K 27/006 119/795 |
| 2006/0084934 A1 | 4/2006 | Frank |
| 2006/0106368 A1 | 5/2006 | Miller et al. |
| 2006/0109086 A1 | 5/2006 | Amtmann |
| 2006/0187044 A1 | 8/2006 | Fabian et al. |
| 2006/0187059 A1* | 8/2006 | Fabian ................... A61B 5/06 340/572.8 |
| 2006/0194899 A1 | 8/2006 | Ohashi et al. |
| 2006/0202827 A1 | 9/2006 | Volpi et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 | 10/2006 | Fabian |
| 2006/0244597 A1 | 11/2006 | Tethrake et al. |
| 2006/0270933 A1 | 11/2006 | Benson et al. |
| 2007/0005141 A1 | 1/2007 | Sherman |
| 2007/0038233 A1 | 2/2007 | Martinez et al. |
| 2007/0051473 A1* | 3/2007 | Speich ............... G08B 13/244 156/384 |
| 2007/0055109 A1 | 3/2007 | Bass et al. |
| 2007/0069866 A1 | 3/2007 | Schuessler et al. |
| 2007/0084550 A1* | 4/2007 | Epstein ................. B29C 65/04 156/272.8 |
| 2007/0125392 A1 | 6/2007 | Olson, Jr. et al. |
| 2007/0209957 A1 | 9/2007 | Glenn et al. |
| 2007/0216062 A1 | 9/2007 | Frank |
| 2007/0219516 A1 | 9/2007 | Patel et al. |
| 2007/0238982 A1 | 10/2007 | Caylor, III |
| 2007/0239982 A1 | 10/2007 | Cambre et al. |
| 2007/0244470 A1 | 10/2007 | Barker, Jr. et al. |
| 2007/0265690 A1 | 11/2007 | Lichtenstein et al. |
| 2007/0270660 A1 | 11/2007 | Caylor, III et al. |
| 2007/0285249 A1 | 12/2007 | Blair et al. |
| 2008/0001760 A1 | 1/2008 | Oh et al. |
| 2008/0007411 A1 | 1/2008 | Levin |
| 2008/0020189 A1* | 1/2008 | Hofmair ................. D06H 1/00 428/190 |
| 2008/0021308 A1 | 1/2008 | Dimmer et al. |
| 2008/0030303 A1 | 2/2008 | Kobren et al. |
| 2008/0051746 A1 | 2/2008 | Shen-Gunther |
| 2008/0086771 A1 | 4/2008 | Li et al. |
| 2008/0126122 A1 | 5/2008 | Warner et al. |
| 2008/0132860 A1* | 6/2008 | Smith ................... A61F 13/44 604/362 |
| 2008/0204245 A1 | 8/2008 | Blair et al. |
| 2008/0231452 A1 | 9/2008 | Levin |
| 2008/0281190 A1 | 11/2008 | Petcavich et al. |
| 2009/0008449 A1 | 1/2009 | Qing et al. |
| 2009/0051485 A1 | 2/2009 | Corry et al. |
| 2009/0267765 A1 | 10/2009 | Greene et al. |
| 2009/0315681 A1 | 12/2009 | Blair |
| 2009/0322485 A1 | 12/2009 | Barnes et al. |
| 2010/0033309 A1 | 2/2010 | Blair |
| 2010/0108079 A1 | 5/2010 | Blair |

(56) References Cited

U.S. PATENT DOCUMENTS

| | | |
|---|---|---|
| 2010/0109848 A1 | 5/2010 | Blair et al. |
| 2011/0004276 A1 | 1/2011 | Blair et al. |
| 2011/0181394 A1 | 7/2011 | Blair |
| 2012/0031547 A1 | 2/2012 | Halberthal et al. |
| 2012/0116499 A1 | 5/2012 | Goetzen et al. |
| 2013/0199720 A1 | 8/2013 | Halberthal et al. |
| 2014/0243770 A1 | 8/2014 | Stewart |
| 2014/0303580 A1 | 10/2014 | Blair |
| 2015/0054625 A1 | 2/2015 | Blair et al. |
| 2015/0164603 A1 | 6/2015 | Fleck et al. |
| 2015/0216610 A1 | 8/2015 | Augustine |
| 2015/0272688 A1 | 10/2015 | Blair et al. |
| 2015/0317555 A1 | 11/2015 | Dor et al. |
| 2016/0157957 A1 | 6/2016 | Blair |
| 2016/0206399 A1 | 7/2016 | Blair |
| 2016/0210548 A1 | 7/2016 | Blair |
| 2016/0250000 A1 | 9/2016 | Blair |

FOREIGN PATENT DOCUMENTS

| | | |
|---|---|---|
| EP | 1612554 A1 | 1/2006 |
| WO | 86/02539 A1 | 5/1986 |
| WO | 02/39917 A1 | 5/2002 |
| WO | 03/073934 A1 | 9/2003 |
| WO | 2006/060781 A1 | 6/2006 |
| WO | 2007/120736 A2 | 10/2007 |
| WO | 2008/008449 A2 | 1/2008 |
| WO | 2008/024921 A1 | 2/2008 |
| WO | 2008/133634 A1 | 11/2008 |
| WO | 2009/154987 A1 | 12/2009 |

OTHER PUBLICATIONS

William Blair, Design U.S. Appl. No. 29/322,539, filed Aug. 6, 2008, 6 pages.

William Blair, U.S. Appl. No. 61/163,813, filed Mar. 26, 2009, 47 pages.

William A. Blair, Design U.S. Appl. No. 29/336,007, filed Apr. 27, 2009, 4 pages.

William A. Blair, Design U.S. Appl. No. 29/336,008, filed Apr. 27, 2009, 7 pages.

William A. Blair, Design U.S. Appl. No. 29/336,009, filed Apr. 27, 2009, 4 pages.

Clearcount Medical Solutions, "The SmartSponge System," Downloaded from http://clearcount.com on Oct. 20, 2009, 7 pages.

Haldor Advanced Technologies, "Haldor Advanced Technologies Releases a Breakthrough New Sponge Management Solution: Modular, Mobile, Wireless, and Tailored per Use-case and Requirements," Sep. 8, 2015, retrieved from http://ww1.prweb.com/prfiles/2015/09/06/12938762/ORLocate%205Sponge%20Solution-September%202015.pdf, 2 pages.

\* cited by examiner

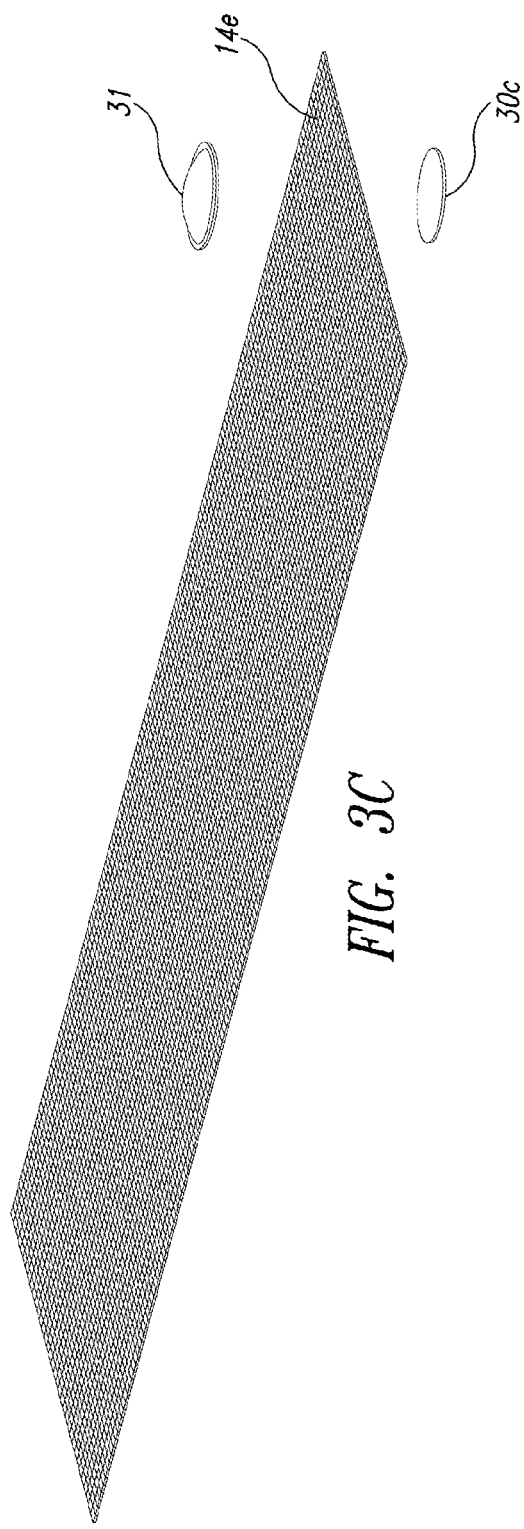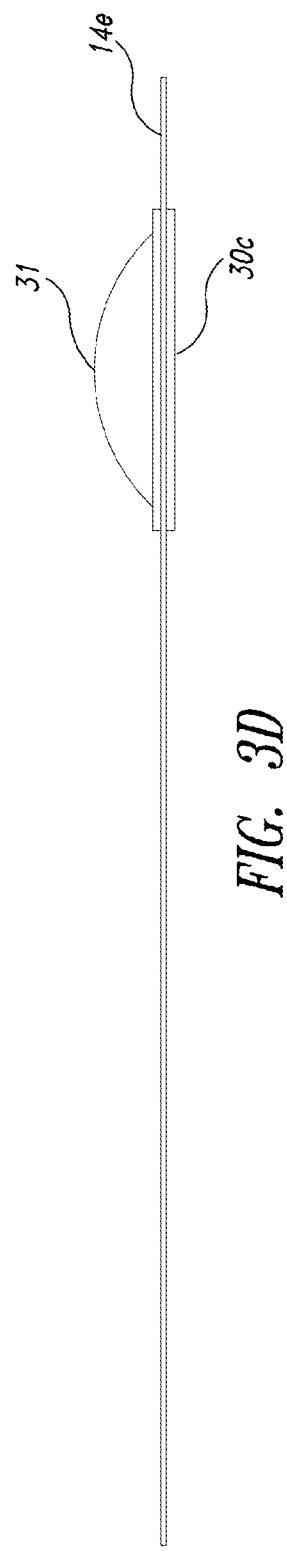

WIRELESSLY DETECTABLE OBJECTS FOR USE IN MEDICAL PROCEDURES AND METHODS OF MAKING SAME

BACKGROUND

Technical Field

This disclosure generally relates to wirelessly detectable objects useful in medical procedures such as surgeries, birth deliveries, and other procedures.

Description of the Related Art

It is often useful or important to be able to determine the presence or absence of a foreign object.

For example, it is important to determine whether objects associated with a medical procedure, for instance surgery, are present in a patient's body before completion of the medical procedure. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures, which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system may include a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost effective and highly accurate. In particular, false negatives must be avoided to ensure that objects are not mistakenly left in the patient. The overall automated system requires a large number of transponders, since at least one transponder is carried, attached or otherwise coupled to each object which may or will be used in surgery. Consequently, the transponders and devices for carrying, attaching or coupling the transponder to the object should be inexpensive. In addition, such inexpensive devices must allow accurate detection and thus not made of metallic materials. Otherwise, if the object and/or the device carrying the transponder is metallic or other metallic objects are present in the body, a transponder that is in fact present may not be able to be detected as a result of the metallic object acting as a Faraday shield or otherwise interfering with transponder communications. The transponder and/or device should be capable of undergoing sterilization.

Moreover, transponders are typically attached or otherwise coupled to individual objects, such as gauzes and lap sponges, one piece of object at a time. That is, a transponder is attached or otherwise coupled to a piece of gauze or lap sponge from a quantity of individual pieces of gauzes or lap sponges. In some cases, this may involve unpacking the gauzes or lap sponges from the package they are provided in before transponders are individually attached or otherwise coupled to each of the gauzes or lap sponges. Further, in certain cases, each piece of gauze or lap sponge may need to be unfolded first before the corresponding transponder is attached to it. These additional steps add undesirable time and costs. Consequently, a new inexpensive device for attaching or otherwise coupling a transponder to an object to be used in a medical procedure, and a new method of attaching or coupling such device and transponder to such an object is highly desirable.

BRIEF SUMMARY

At least one embodiment may be summarized as a wirelessly detectable object for use in medical procedures, which object includes a piece of absorbent material, a transponder to wirelessly receive and transmit signals, and a cover having a receiving cavity to receive the transponder. The cover may be attached directly to the piece of absorbent material to enclose the transponder therebetween. The piece of absorbent material may be a sponge. The piece of absorbent material may be a piece of gauze. The cover may be made of polyvinyl chloride (PVC).

A radio frequency (RF) weld may attach the cover to the piece of absorbent material. The detectable surgical object may further include stitching that attaches the cover to the piece of absorbent material.

At least one embodiment may be summarized as a wirelessly detectable object for use in medical procedures, which object includes a piece of absorbent material, a transponder to wirelessly receive and transmit signals, and a flexible sheet attached directly to the piece of absorbent material and forming a pocket to enclose the transponder therein. The piece of absorbent material may be a sponge. The piece of absorbent material may be a piece of gauze. The flexible sheet may be a sheet of PVC impregnated cotton fabric. The transponder may be sealed in the pocket formed by the flexible sheet by RF welding.

An RF weld may seal the transponder in the pocket formed by the flexible sheet, and stitching that attaches the pocket formed by the flexible sheet to the piece of absorbent material.

The wirelessly detectable disposable object may be a disposable surgical object where the piece of absorbent material has at least one edge and has a first surface and a second surface opposite to the first surface, wherein the flexible sheet is folded over one of the at least one edge of the piece of absorbent material to provide a first portion of the flexible sheet adjacent the first surface of the piece of absorbent material and a second portion of the flexible sheet adjacent the second surface of the piece of absorbent material, and wherein the first portion of the flexible sheet is further folded to form the pocket enclosing the transponder therein. The first and the second portions of the flexible sheet may be RF welded to the piece of absorbent material.

At least one embodiment may be summarized as a wirelessly detectable object for use in medical procedures, which object includes a piece of absorbent material, a transponder to wirelessly receive and transmit signals, and a container containing the transponder and attached directly to the piece of absorbent material. The piece of absorbent material may be a sponge. The piece of absorbent material may be a piece of gauze.

The wirelessly detectable object may further include an RF weld that attaches the container to the piece of absorbent material. The wirelessly detectable object may further include a radio-opaque strip carried by the piece of absorbent material, and the radio-opaque strip may be a strip of blue barium. The wirelessly detectable object may further include an RF weld that attaches the container directly to the radio-opaque strip. The wirelessly detectable object may further include stitching that attaches the container directly to the radio-opaque strip.

The wirelessly detectable object may be a disposable surgical object where the container includes first, second, and third members, wherein the piece of absorbent material has first and second surfaces opposite to each other, wherein the first member has a cavity to receive the transponder, wherein the first and second members form a pouch to contain the transponder, and wherein the pouch containing the transponder is attached to the first surface of the piece of absorbent material and the third member is attached to the second surface of the piece of absorbent material directly opposite the pouch. The first, second, and third members of the container may be made of PVC. The pouch and the third member may be attached to the piece of absorbent material by RF welding.

At least one embodiment may be summarized as a wirelessly detectable object for use in medical procedures. The medical procedure may, for instance be a surgical procedure. The object may include a transponder to wirelessly receive and transmit signals, a flexible sheet forming a cavity, and at least one RF weld that seals the transponder in the cavity. The flexible sheet may be attached directly to the object. The object may include a piece of absorbent material, which may be a sponge. The piece of absorbent material may be a piece of gauze. The flexible sheet may be made of PVC or may be a piece of PVC impregnated cotton fabric. The flexible sheet may be attached directly to the object by the at least one RF weld.

The wirelessly detectable object may further include stitching that attaches the flexible sheet directly to the object.

At least one embodiment may be summarized as a method of manufacturing a plurality of wirelessly detectable objects for use in medical procedures, including attaching a plurality of transponders to a substantially flat object; and dividing the substantially flat object to provide a plurality of discrete objects each having a respective one of the plurality of transponders attached thereto. Attaching a plurality of transponders to a roll of absorbent material may include attaching a plurality of transponders to a roll of gauze. Dividing the roll of absorbent material into a plurality of discrete pieces of absorbent material each having a respective one of the plurality of transponders attached thereto may include dividing the roll of gauze to provide a plurality of discrete pieces of gauze each having a respective one of the plurality of transponders attached thereto.

According to at least one embodiment, attaching a plurality of transponders to a roll of absorbent material may include RF welding a plurality of transponders to the roll of absorbent material.

The method may further include providing a plurality of housing objects each having a cavity to hold a respective one of the plurality of transponders, and sealing each of the transponders in the cavity of the respective one of the housing objects by RF welding. Attaching a plurality of transponders to a roll of absorbent material may include attaching the plurality of housing objects each containing a respective transponder to the roll of absorbent material. Providing a plurality of housing objects each having a cavity to hold a respective one of the plurality of transponders may include providing a plurality of sheets of flexible material each forming a pocket to hold a respective one of the plurality of transponders. RF welding the housing objects to seal each of the transponders in the cavity of the respective one of the housing objects may include RF welding the sheets of flexible material to seal each of the transponders in the pocket of the respective one of the sheets of flexible material.

According to at least one embodiment, attaching the plurality of housing objects each containing a respective transponder to the roll of absorbent material may include RF welding the plurality of sheets of flexible material each containing a respective transponder to the roll of absorbent material. Attaching the plurality of housing objects each containing a respective transponder to the roll of absorbent material may also be sewing the plurality of sheets of flexible material each containing a respective transponder to the roll of absorbent material. Providing a plurality of housing objects may include providing housing objects made of PVC impregnated cotton fabric or PVC.

The method may further include providing a roll of absorbent material pouches each containing a respective one of the plurality of transponders and RF welded to seal the respective transponder within, and separating the roll of absorbent material pouches into individual fabric pouches each containing a respective one of the plurality of transponders. Attaching a plurality of transponders to a roll of absorbent material may include RF welding the fabric pouches to the roll of absorbent material.

The method may further include packaging at least one of the plurality of discrete pieces of absorbent material having a respective transponder attached thereto. The method may also include testing the at least one packaged discrete piece of absorbent material having a respective transponder attached thereto.

At least one embodiment may be summarized as a method of manufacturing a wirelessly detectable object for use in medical procedures, the method including enclosing a transponder in a receiving cavity of a flexible holder by heat sealing; and attaching the flexible holder to an object. Enclosing a transponder in a receiving cavity of a flexible holder may include enclosing the transponder in the receiving cavity of the flexible holder made of PVC or forming a pocket with a piece of PVC impregnated cotton fabric to receive the transponder and enclosing the transponder in the pocket. Enclosing a transponder in a receiving cavity of a flexible holder by heat sealing may include sealing the transponder in the pocket formed from the PVC impregnated cotton fabric by RF welding, and attaching the flexible holder to a surgical object may include attaching the pocket containing the sealed transponder to the object by RF welding. Enclosing a transponder in a receiving cavity of a flexible holder by heat sealing may include sealing the transponder in the pocket formed from the PVC impregnated cotton fabric using RF welding, and wherein attaching the flexible holder to an object comprises attaching the pocket containing the sealed transponder to the object by sewing.

According to at least one embodiment, attaching the flexible holder to an object may include attaching the flexible holder to a sheet of gauze or a sponge. Enclosing a transponder in a receiving cavity of a flexible holder by heat sealing may include sealing the transponder between a first member of the flexible holder and a second member of the flexible holder having a receiving cavity to receive the transponder by RF welding. Attaching the flexible holder to an object may include RF welding the flexible holder containing the transponder to a radio-opaque strip on a sheet of lap sponge, which may include RF welding the flexible holder containing the transponder to a strip of blue barium on the sponge. Attaching the flexible holder to an object may include sewing the flexible holder containing the transponder to a radio-opaque strip on a sponge. Sewing the flexible holder containing the transponder to a radio-opaque strip on a sheet of lap sponge may include sewing the flexible holder containing the transponder to a strip of blue barium on the sheet of lap sponge.

According to at least one embodiment, enclosing a transponder in a receiving cavity of a flexible holder may include enclosing each of a plurality of transponders in a respective one of a plurality of fabric pouches, the plurality of fabric pouches being part of a roll of the fabric pouches. Attaching the flexible holder to an object may include separating the roll of fabric pouches into individual fabric pouches each containing a respective one of the plurality of transponders; RF welding the fabric pouches to a roll of gauze; and separating the roll of gauze into a plurality of individual pieces of gauze each having a respective fabric pouch attached thereto and containing a respective transponder.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 3C is an isometric view of an assembly of a transponder device and an object to be used in medical procedures, according to one embodiment.

FIG. 3D is a side view of the assembly of an object to be used in medical procedures with the transponder device attached thereto of FIG. 3C.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers, and types of objects employed in medical procedures, for instance sponges, gauze or other absorbent objects, have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

For ease of understanding, a surgical environment will be used as an example environment for detecting objects but such should not be considered limiting.

Figure 1:
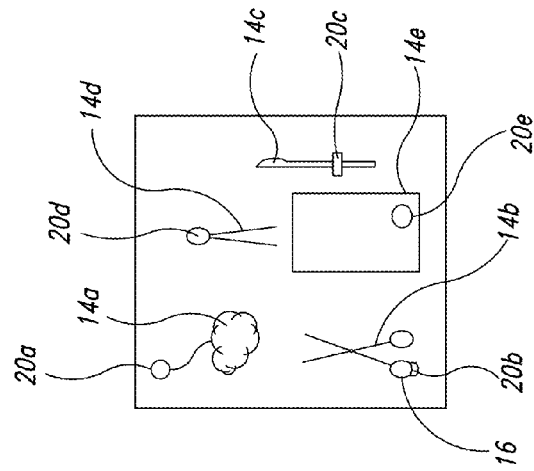
FIG. 1 is a schematic diagram showing an environment in which medical procedures are preformed, for instance a surgical environment, illustrating use of an interrogation and detection system to detect one or more wireless detectable objects tagged with transponder(s), to prevent the objects from inadvertently being left behind in a patient, according to one illustrated embodiment.
Figure 1:
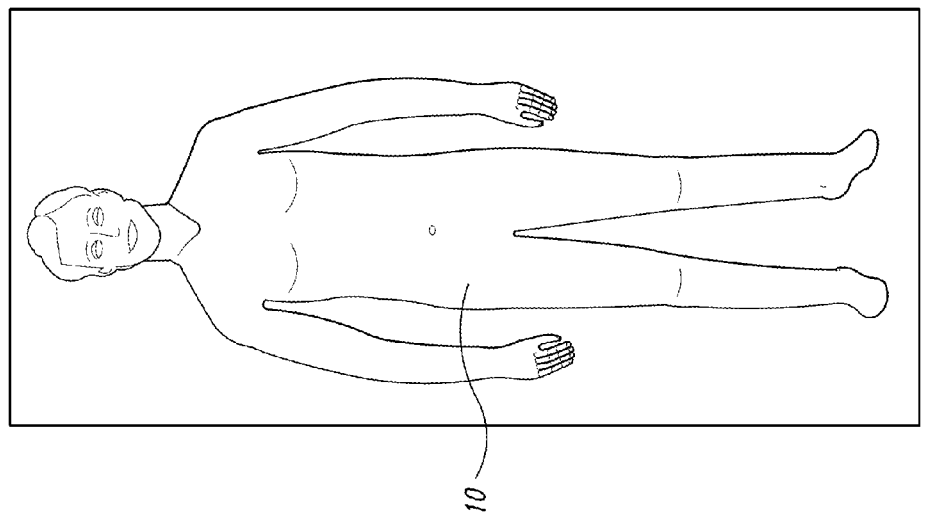
Figure 1:
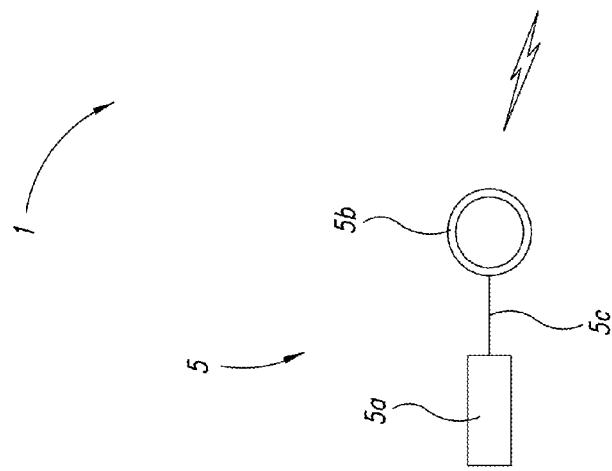

FIG. 1 shows an environment 1 in which medical procedures are performed, for example a surgical environment, clinician's office, examination room, patient room or other environments in which medical procedures may be performed. A medical provider (not shown) operates an interrogation and detection system 5 to ascertain the presence or absence of objects in, or on, a patient 10.

The interrogation and detection system 5 may include a controller 5a and an antenna 5b. The antenna 5b is coupled to the controller 5a by one or more communication paths, for example a coaxial cable 5c. The antenna 5b may take the form of a hand-held wand. The controller 5a is configured to cause the antenna to emit wireless interrogation signals in one or more wide frequency bands, to receive responses from transponders to such interrogation signals, and to determine the presence or absence of a transponder based on the received responses, if any.

The environment 1 may include a number of objects, collectively 14, used or employed when performing medical procedures. For instance, the objects may include surgical objects 14 used in performing surgical procedures. The objects 14 may take a variety of forms, for example instruments, accessories and/or disposable objects useful in performing medical procedures. Each object 14 is tagged, attached, or otherwise coupled with a transponder device, collectively 20, and therefore detectable by the interrogation and detection system 5. Thus, medical procedure objects 14a-14e may each be associated with a respective transponder device 20a-20e, making those objects 14 wirelessly detectable.

The transponder devices 20 each include a respective transponder 38. The transponder 38 may be constructed in various manners. For example, the transponder 38 may include a ferrite rod with a conductive coil wrapped about an exterior surface thereof to form an inductor, and a capacitor coupled to the conductive coil to form a series circuit. The conductive coil may, for example, take the form of a spiral wound conductive wire with an electrically insulative sheath or sleeve. Additional details about types of transponders may be found in U.S. Provisional Patent Application Ser. No. 60/811,376 filed Jun. 6, 2006 and U.S. Provisional Patent Application Ser. No. 60/892,208, filed Feb. 28, 2007.

The transponder 38 is typically small, for example approximately 5-10 millimeters long with a diameter of about 1-4 millimeters. In at least some embodiments, an encapsulant 30 advantageously protects the transponder from the ambient environment, for instance from forces, pressure and/or fluids, such as body fluids.

The objects 14 that may be tagged with a respective transponder 38 to be detectable by the interrogation and detection system 5 may be any type of object useful in a medical procedures, for instance medical implements (e.g., surgical implements) as well as medical supplies or accessories (e.g., surgical supplies or accessories). Examples of various types of medical implements include, but are not limited to, cutting means (e.g., a scalpel 20c, lancet, knife, scissors), grasping means (e.g., tweezers 14d, forceps), clamping means (e.g., hemostat 14b, clamps), access means (e.g., dilators, specula, separators), injection/irrigation means (e.g., needles, tips), drilling means (e.g., a drill bit), or measurement means (e.g., rulers, calipers).

Examples of various types of medical supplies or accessories include, but are not limited to, sponge 14a and a sheet of absorbent material 14e. The sheet of absorbent material 14e may be a piece of gauze or a piece of lap sponge, which may be woven or unwoven, for example. As shown in FIG. 1, the sheet of absorbent material 14e may be tagged with a transponder device 20 so that the presence or absence of the sheet of absorbent material 14e can be detected by the interrogation and detection system 5. Again, this helps achieve the goal of avoiding foreign objects, including the sheet of absorbent material 14e, from being unintentionally left at an undesirable location, such as inside the body of a patient 10, after surgery, child birth or delivery, or other medical procedures.

In use, the medical provider (not shown) may position the antenna 5b proximate the patient 10 in order to detect the presence or absence of the transponder 38 and hence a foreign object. The medical professional may in some embodiments move the antenna 5b along and/or across the body of the patient 10. In some embodiments, the antenna 5b may be sized to fit at least partially in a body cavity of the patient 10. Different types of transponders 38 may be used. Although a human patient 10 is illustrated, the described interrogation and detection system 1 may similarly be used on animals.

Figure 2A:
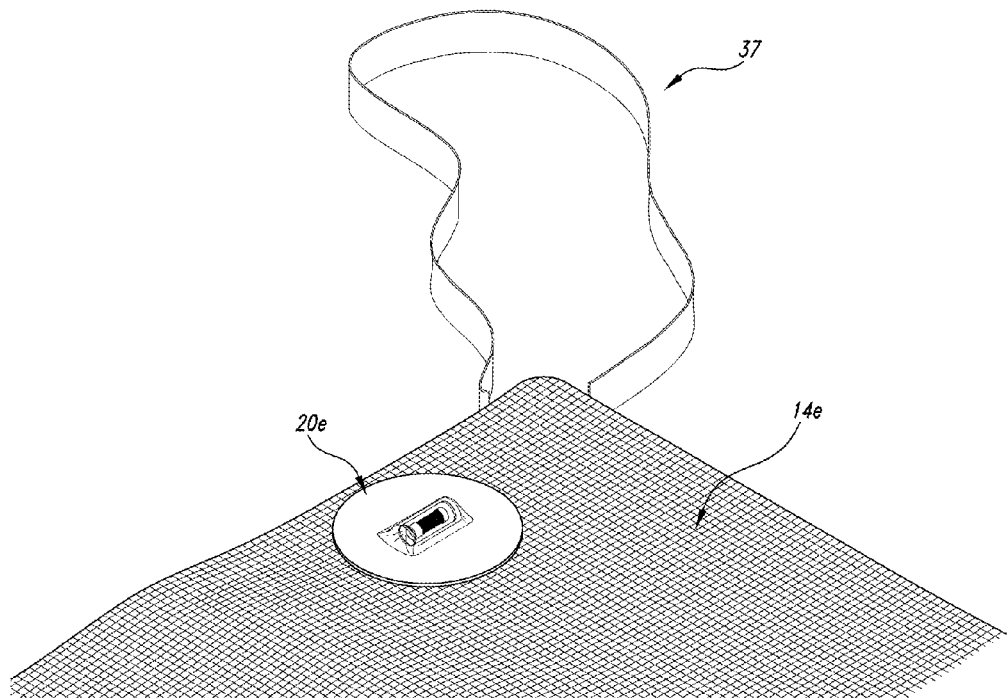
FIG. 2A is a diagram of a transponder device attached to an object to be used in medical procedures, according to one illustrated embodiment.

FIG. 2A illustrates a transponder device 20e attached to an object 14e to be used in a medical procedure, according to one embodiment. Since the object 14e may be useful in performing medical procedures, the object 14e may be denominated as a medical object or medical procedure object.

The transponder device 20e is advantageously attached to a portion of the object 14e such that the transponder device 20e does not physically interfere with the operation or use of the object 14e. The object 14e may be a piece of absorbent material, such as a piece of gauze or lap sponge. Such objects 14e are typically disposed of after use, so may be denominated as disposable objects, or disposable medical objects, or disposable medical procedure objects. Such objects 14e are typically considered medical supplies so may be denominated as a medical supply or disposable medical supply.

The object 14e may include a strap or loop 37 to facilitate carrying, moving and/or tactilely locating the object 14e. The transponder device 20e may comprise an encapsulant or cover 30 and a transponder 38 to retain the transponder 38. The encapsulant or cover 30 may include one or more structures designed and configured to enclose the transponder 38 and directly attach the transponder 38 to a portion of the object 14e. The encapsulant or cover 30 may be a plastic housing made of polyvinyl chloride (PVC). Alternatively, the encapsulant or cover 30 may be made of PVC impregnated cotton fabric. While the term encapsulant is used herein, such should not be confused with encapsulants typically used to provide environmental protection to a circuit or chip. Such encapsulants are often made of glass or ceramic, and are not typically used to directly attach a circuit or chip to another structure. As illustrated FIGS. 2B and 3A, such an environmental encapsulant 29 may be used in addition to the encapsulant or cover 30 discussed herein.

Figure 2B:
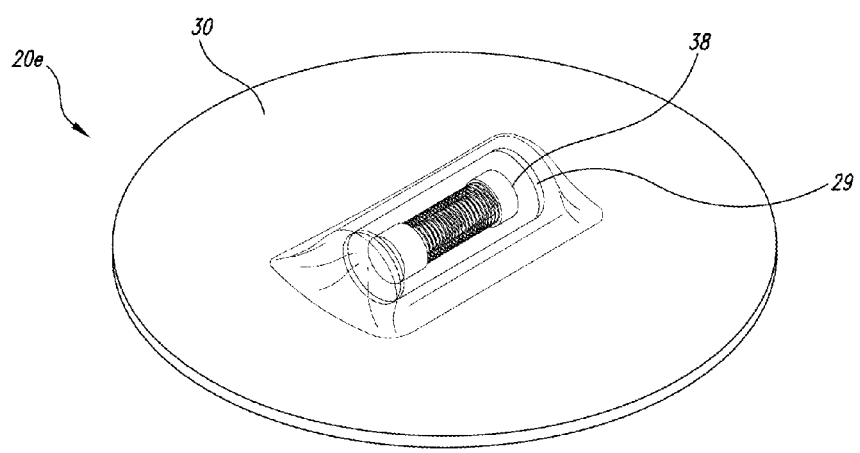
FIG. 2B is a diagram of a transponder housing that receives and couples the transponder to the object, according to one illustrated embodiment.

FIG. 2B illustrates the encapsulant 30 of the transponder device 20e according to one embodiment.

The encapsulant or cover 30 may be a PVC cover designed to have a receiving cavity that is sized and shaped appropriately to receive the transponder 38 such that the transponder 38 fits snugly in the receiving cavity of the encapsulant 30. Alternatively, the encapsulant or cover 30 may adapt a different shape and size. For example, the encapsulant or cover 30 may have a dome shape or any other shape. In one embodiment, the encapsulant or cover 30 may be a one-piece cover, and the transponder 38 may be enclosed between the enclosed space between the encapsulant or cover 30 and the object 14e when the encapsulant or cover 30 is attached directly to the object 14e. The encapsulant or cover 30 may be heat sealed to the object 14e to seal the transponder 38 between the encapsulant or cover 30 and the object 14e. In one embodiment, the encapsulant or cover 30 may be radio frequency (RF) welded to the object 14e to seal the transponder 38 between the encapsulant or cover 30 and the object 14e. Alternatively, the encapsulant or cover 30 may be sewn to the object 14e by stitching to seal the transponder therebetween.

Figure 3A:
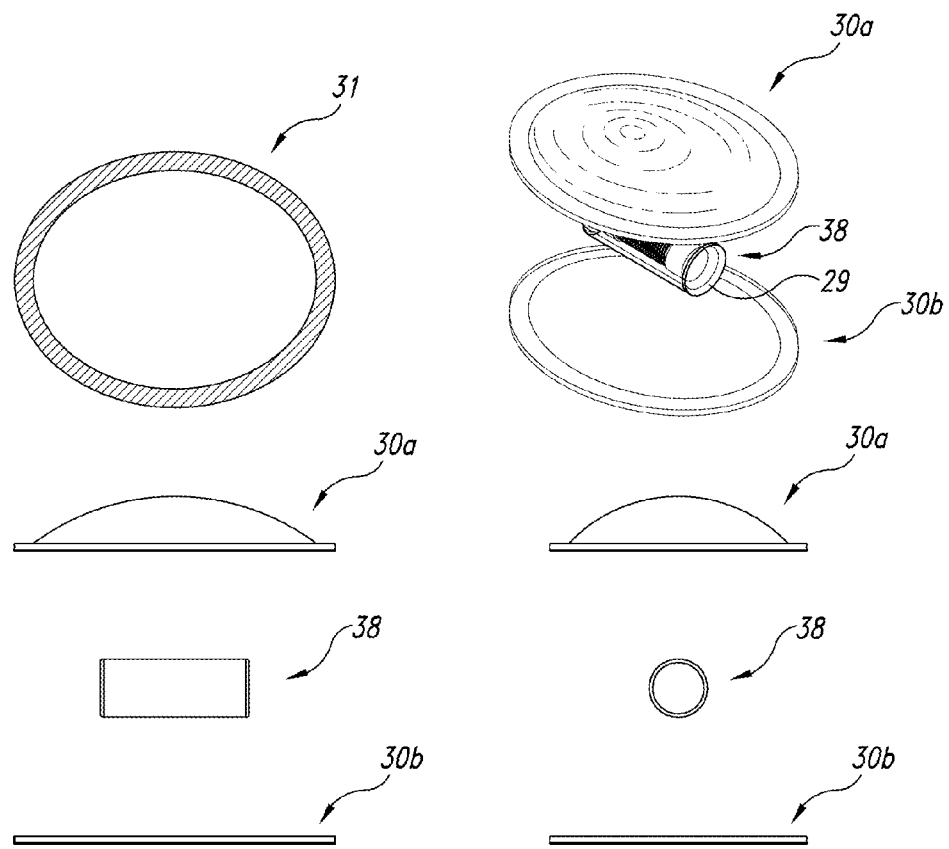
FIG. 3A is a diagram of a transponder device, according to one illustrated embodiment.

FIG. 3A illustrates the transponder device 20e according to one embodiment.

In this illustrated embodiment, the transponder device 20e includes a container 30 formed from three body portions 30a, 30b, and 30c (FIG. 3C). The body portion 30a may be a cover member made of PVC having a dome-shaped cavity in which the transponder 38 may be received. The body portion 30b may be a PVC film sized and shaped to match the outer contour of the body portion 30a. The body portion 30c may also be made of PVC and, like the body portion 30b, may be sized and shaped to match the outer contour of the body portion 30a. Alternatively, the body portions 30a, 30b, and 30c may be made of PVC impregnated cotton fabric.

As shown in FIG. 3A, the transponder 38 is received in the dome-shaped cavity of the body portion or cover 30a and is enclosed by the body portions 30a and 30b. Sealing of the transponder 38 within the enclosed space between the body portions 30a and 30b may be done by a variety of sealing methods including heat sealing. A type of heat sealing method that may be used is RF welding. Thus, in one embodiment, the transponder 38 may be RF welded within the enclosed space between the body portions 30a and 30b. The combination of the body portion 30a, the transponder 38, and the body portion 30b is labeled as the transponder pouch 31. In some embodiments, formation of the transponder pouch 31 (i.e., sealing the transponder 38 between the body portions 30a and 30b) may be done in advance. More specifically, transponder pouches 31 may be made available prior to further manufacturing process is undertaken to the wirelessly detectable objects from the objects 14e and the transponder devices 20e.

Figure 3B:
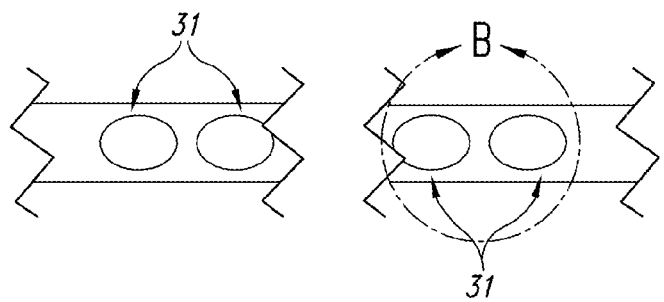
FIG. 3B is a diagram of a transponder device, according to another illustrated embodiment.
Figure 3B:
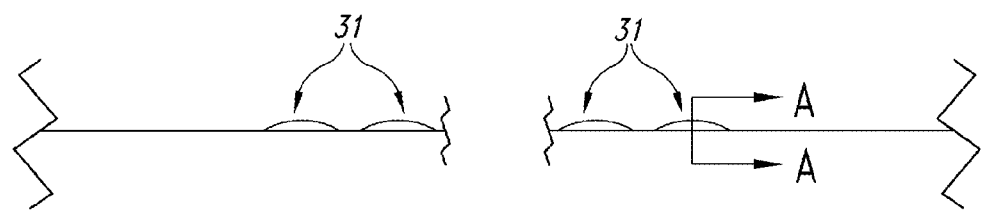
Figure 3B:
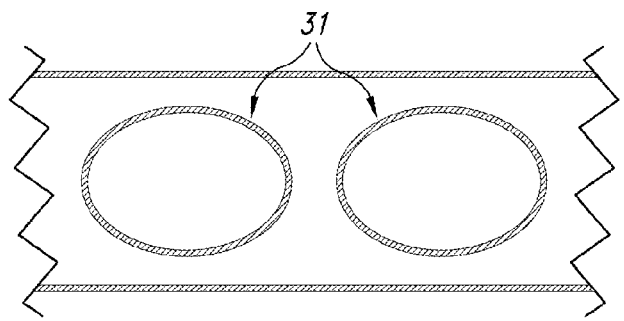
Figure 3B:
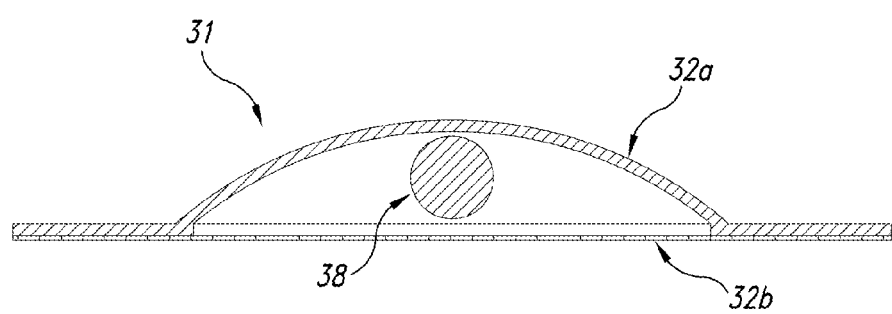

FIG. 3B illustrates the transponder device 20e according to another embodiment.

Rather than being discretely made from the assembly of individual components, the transponder pouch 31 may come as a roll of transponder pouches 31 each containing a respective transponder 38, as shown in FIG. 3B. The roll of transponder pouches 31 may be made by RF welding a roll of fabric laminate 32a to a roll of PVC film 32b where a series of cavities for receiving a corresponding transponder 38 is made by providing bulges in the roll of fabric laminate 32a. The fabric laminate 32a may be made of PVC or PVC impregnated cotton fabric. Having the transponder pouches 31 come in a roll enhances the efficiency in the manufacturing process, as all that remains to be done is cutting or separating the transponder pouches from the roll and attaching each of the transponder pouches to a respective object 14e.

FIG. 3C illustrates an isometric view of the assembly of the transponder device 20e and object 14e to be used in medical procedures, according to one embodiment.

As shown in FIG. 3C, the transponder pouch 31, whether assembled individually with body portions 30a and 30b or provided as part of a roll of transponder pouches, may be RF welded to a surface of the object 14e. The body portion 30c is placed on the other surface of the object 14e directly opposite the transponder pouch 31 so that the transponder device 20e can be RF welded to the object 14e.

FIG. 3D illustrates a side view of the disposable object 14e to be used in medical procedures with the transponder device 20e attached thereto, according to one embodiment.

Figure 4A:
FIG. 4A is a diagram of a method of attaching a transponder device to an object to be used in medical procedures, according to one embodiment.
Figure 4A:
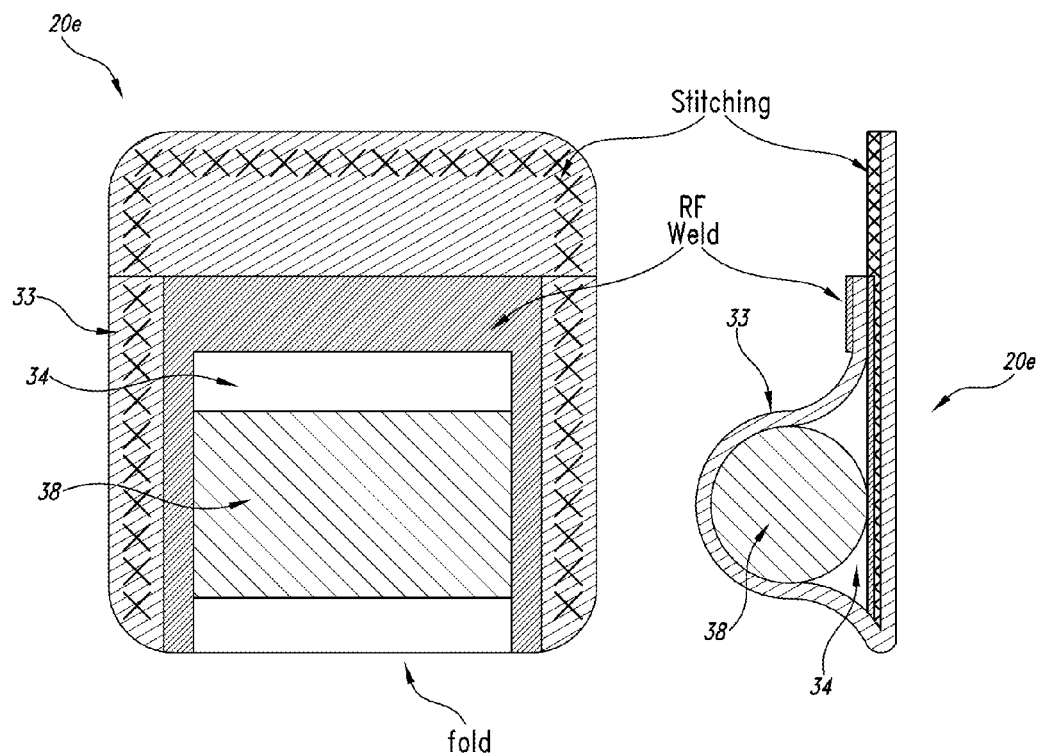

FIG. 4A illustrates a method of attaching the transponder device 20e to the object 14e to be used in medical procedures, according to one embodiment.

The encapsulant or cover 30 of the transponder device 20e in this embodiment may be a flexible sheet 33 made from a piece of PVC impregnated cotton fabric. Thus, the transponder device 20e in this embodiment includes the transponder 38 and the flexible sheet 33. As shown in FIG. 4A, the flexible sheet 33 is folded to form a pouch having a pocket 34 to receive the transponder 38, and the transponder 38 is enclosed in the pocket 34. The transponder 38 is sealed in the pocket 34 by heat sealing, e.g., RF welding, around at least three sides of the transponder 38. That is, as shown in FIG. 4A, because one side of the transponder 38 is adjacent the fold in the flexible sheet 33, RF welding is used to seal the remaining three sides of the transponder 38.

The transponder device 20e may be attached to the object 14e, such as a piece of gauze or lap sponge, by sewing. For example, the transponder device 20e may be sewn to the object 14e by stitching in one embodiment. To prevent the transponder device 20e from dangling, e.g., when the object 14 with the transponder device 20e attached is held up in such a fashion that the transponder device 20e is facing downward, at least two lines of stitches are used to attach the transponder device 20e to the object 14e. The two lines of stitches may be perpendicular to the fold line where the flexible sheet 33 is folded to form the pocket 34. Alternatively, three lines of stitches may be used, as shown in FIG. 4A, to ensure the pouch formed by the folded flexible sheet 33 does not dangle. In such case, two of the lines of stitches may be perpendicular to the fold line while the third line of stitches may be parallel to the fold line, as shown in FIG. 4A. In other embodiments, the transponder device 20e may be attached to the object 14e by heat sealing, such as RF welding, or other suitable methods.

Figure 4B:
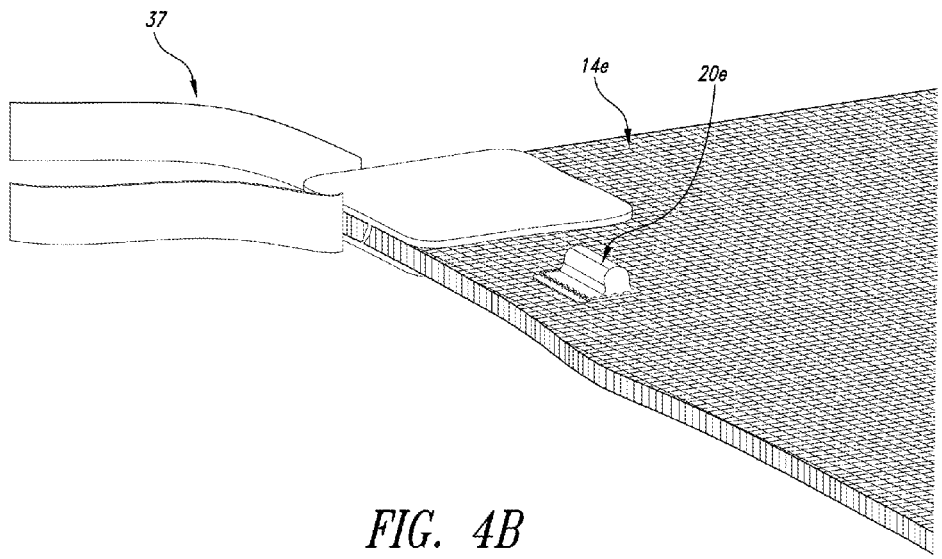
FIG. 4B is a diagram of an object to be used in medical procedures, having a transponder device attached thereto according to the method shown in FIG. 4A.

FIG. 4B illustrates the object 14e to be used in medical procedures having the transponder device 20e attached thereto, according to the method shown in FIG. 4A.

Figure 5B:
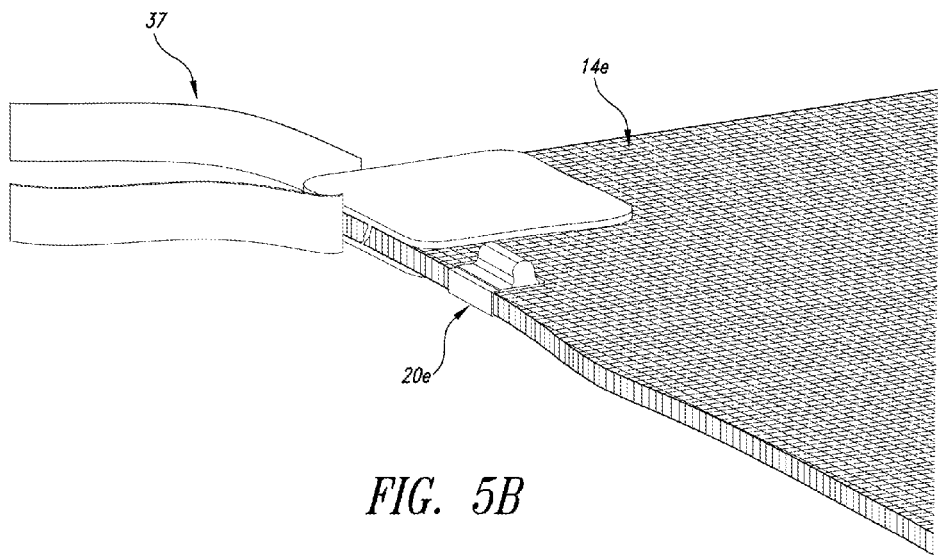
FIG. 5B is a diagram of an object to be used in medical procedures having a transponder device attached thereto, according to the method shown in FIG. 5A.
Figure 5A:
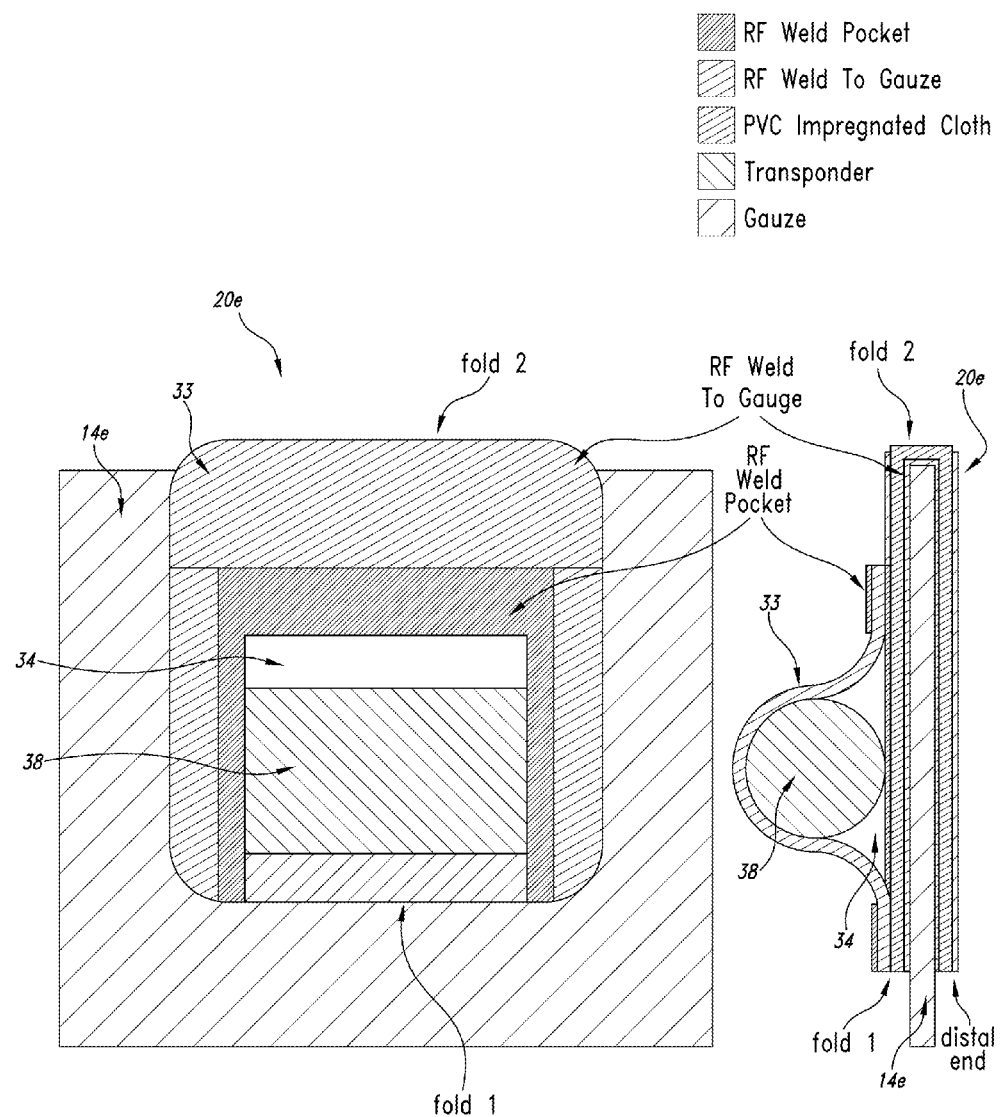
FIG. 5A is a diagram of a method of attaching a transponder device to an object to be used in medical procedures, according to another embodiment.

FIG. 5A illustrates a method of attaching the transponder device 20e to the object 14e to be used in medical procedures, according to another embodiment.

The encapsulant or cover 30 of the transponder device 20e in this embodiment may be a flexible sheet 33 made from a piece of PVC impregnated cotton fabric. Similar to the transponder device 20e shown in FIG. 4A, the transponder device 20e in this embodiment includes the transponder 38 and the flexible sheet 33. As shown in FIG. 5A, the flexible sheet 33 is folded to form a pouch having a pocket 34 to receive the transponder 38, and the transponder 38 is enclosed in the pocket 34. The transponder 38 is sealed in the pocket 34 by heat sealing, e.g., RF welding, around at least three sides of the transponder 38. That is, as shown in FIG. 4A, because one side of the transponder 38 is adjacent the fold in the flexible sheet 33, RF welding is used to seal the remaining three sides of the transponder 38.

The flexible sheet 33 is further folded to wrap around an edge of the object 14e. More specifically, the size and dimension of the flexible sheet 33 are chosen so that after a first fold (fold 1 shown in FIG. 5A) to form the pocket 34 and a second fold (fold 2 shown in FIG. 5A) to wrap around an edge of the object 14e, the distal end of the flexible sheet 33 is approximately aligned with the first fold, or fold 1. In other words, in this embodiment, the flexible sheet 33 is folded to enclose the transponder 38 as well as to "clamp on" an edge of the object 14e, which may be a piece of gauze of lap sponge. To secure the transponder device 20e to the object 14e, RF welding may be used, as shown in FIG. 5A.

Alternatively, the transponder device 20e may be attached to the object 14e by other means including sewing and other heat sealing methods.

FIG. 5B illustrates the object 14e to be used in medical procedures having the transponder device 20e attached thereto, according to the method shown in FIG. 5A.

Figure 6A:
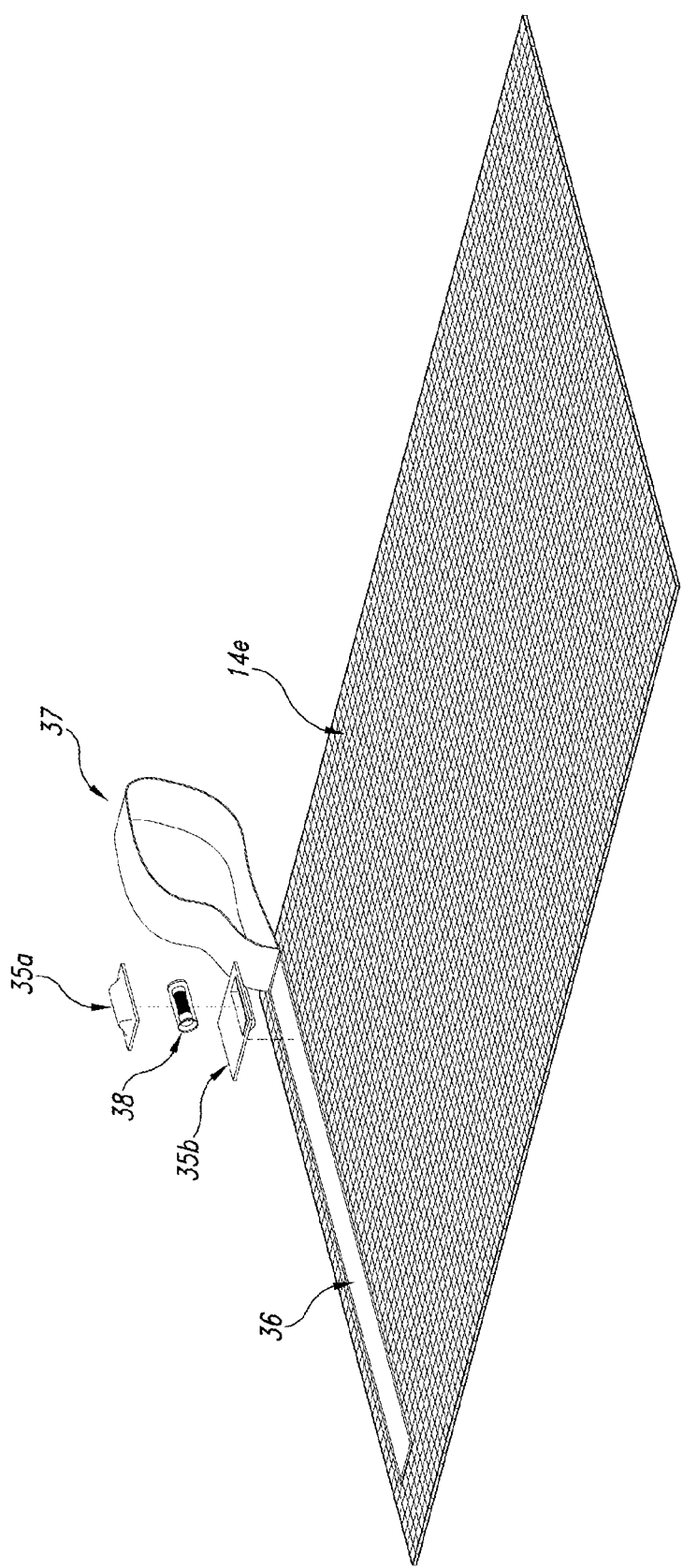
FIG. 6A is a diagram of a method of attaching a transponder device to an object to be used in medical procedures, according to yet another embodiment.

FIG. 6A illustrates a method of attaching the transponder device 20e to the object 14e to be used in medical procedures, according to yet another embodiment.

Figure 6B:
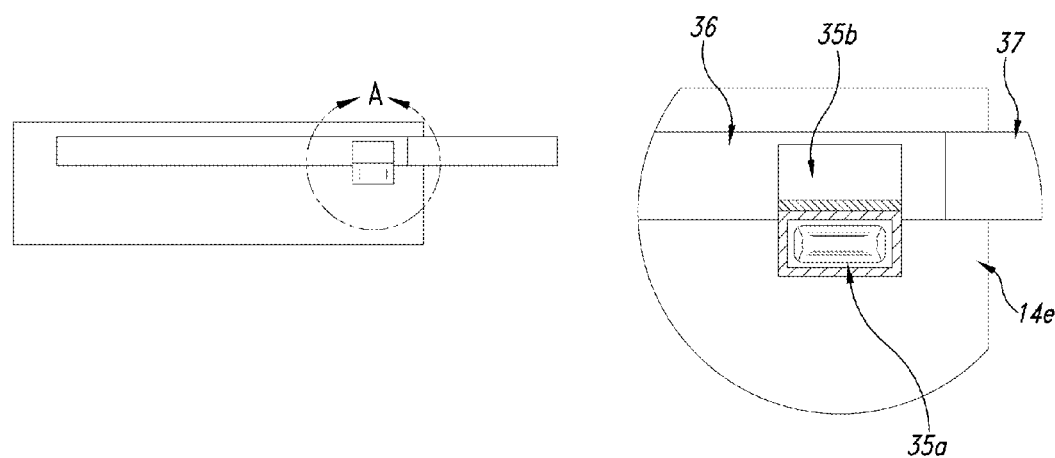
FIG. 6B is a diagram showing the attachment of a transponder device to an object to be used in medical procedures, according to the method shown in FIG. 6A.

The encapsulant or cover 30 of the transponder device 20e in this embodiment may include a top portion 35a and a bottom portion 35b each made from PVC. Thus, the transponder device 20e in this embodiment includes the transponder 38 and the top and bottom portions 35a and 35b. The top portion 35a may be designed and shaped to include a receiving cavity to receive the transponder 38. The bottom portion 35b may be relatively flat and longer than the top portion 35a in at least one dimension to provide for a "tab" portion to allow the transponder device 20e to be attached to the object 14e to be used in medical procedures. As shown in FIG. 6A, the transponder 38 is enclosed between the top portion 35a and the bottom portion 35b. As shown in FIG. 6B, the transponder 38 may be sealed in the enclosed space between the top and bottom portions 35a and 35b by RF welding or other heat sealing method.

The object 14e may include a radio-opaque strip 36, such as a strip of blue barium or PVC material, to which the transponder device 20e may be attached. The object 14e may further include a strap 37 for ease of carrying by a user. The object 14e may be a lap sponge, for example, or another type of absorbent material such as gauze, which is typically disposed of after use.

FIG. 6B illustrates the attachment of the transponder device 20e to the object 14e to be used in medical procedures, according to the embodiment as shown in FIG. 6A.

As previously described, the transponder device 20e may have a "tab" given the difference in size and dimension between the top portion 35a and the bottom portion 35b. Consequently, the transponder device 20e may be attached to the radio-opaque strip 36 of the object 14e by stitching or heat sealing, such as RF welding, or both.

Figure 7:
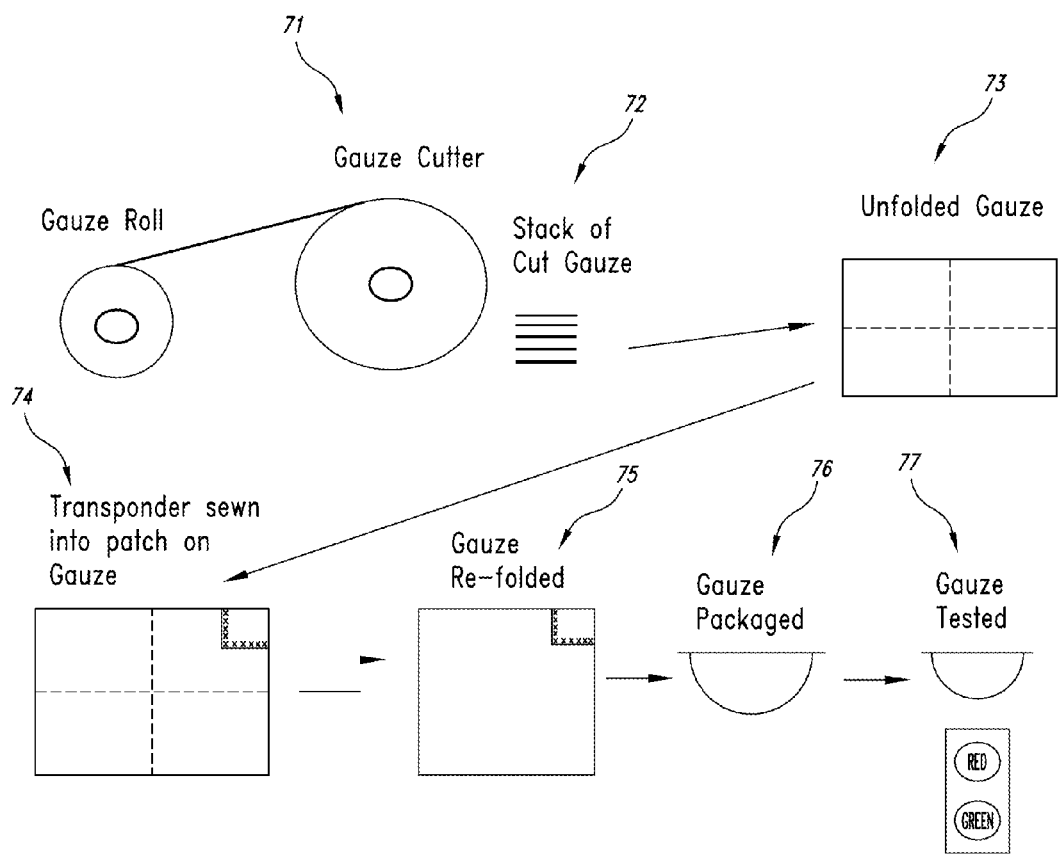
FIG. 7 is a diagram of a conventional process of manufacturing wirelessly detectable objects to be used in medical procedures.

FIG. 7 illustrates a conventional process of manufacturing wirelessly detectable objects for use in medical procedures, such as pieces of gauze 14e each with a transponder device 20e attached thereto.

The process begins with passing a roll of gauze through a gauze cutter that cuts the roll of gauze into a plurality of discrete pieces of cut gauze 14e at 71. The discrete pieces of cut gauze 14e may be folded and piled into one or more stacks of gauze at 72 for further processing. For example, the pieces of cut gauze 14e may be transported to another location in the factory where the roll of gauze was cut or another factory or geographic location. Folding the pieces of cut gauze 14e may render the transportation of the pieces of cut gauze 14e easier than otherwise. Next, at 73, each piece of the cut gauze 14e may need to be unfolded to allow a transponder to be attached thereto. A transponder device 20e may be attached to a respective piece of cut gauze 14e by sewing the transponder device 20e in a patch at 74. Afterwards, the pieces of cut gauze 14e may be refolded at 75 for packaging at 76. With a transponder device 20e attached, each piece of cut gauze 14e becomes a wirelessly detectable object for use in medical procedures. The wirelessly detectable objects may be tested for operability at 77 before they are sold, distributed, or used.

Figure 8:
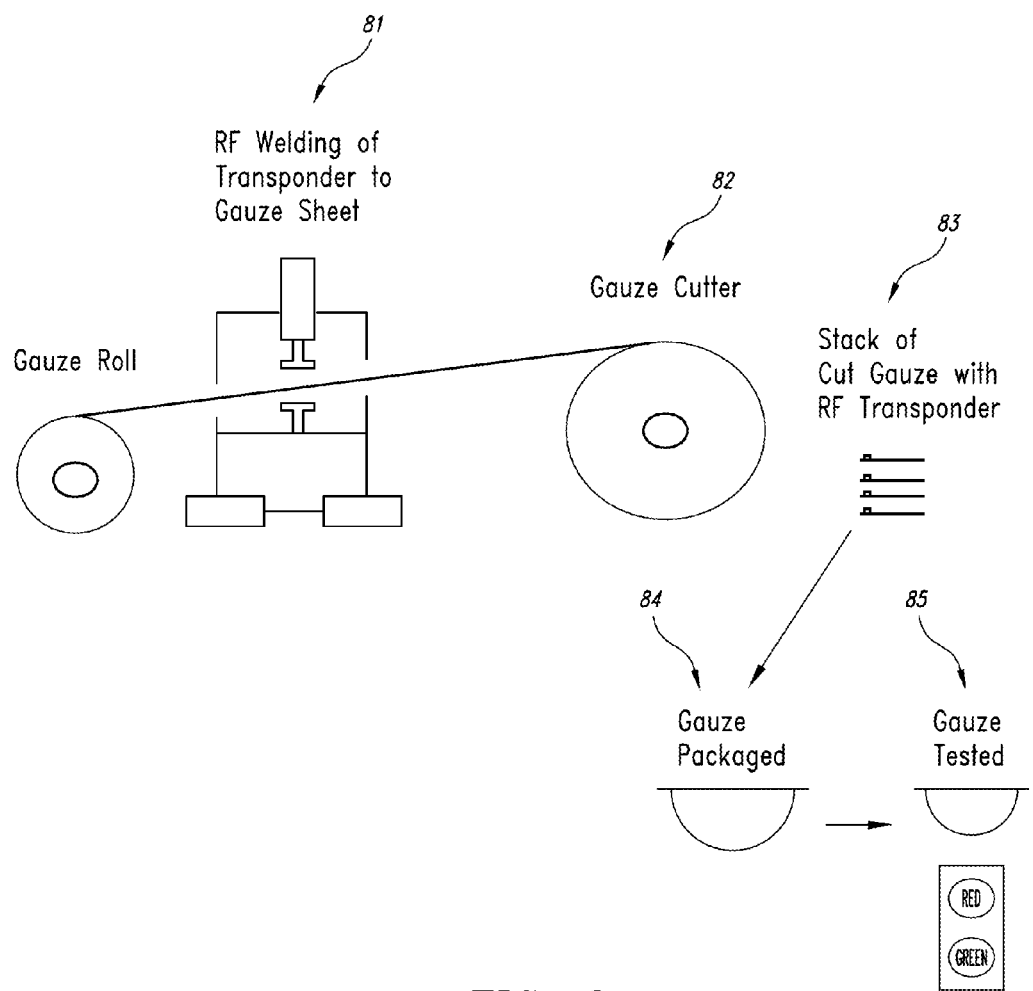
FIG. 8 is a diagram of a process of manufacturing wirelessly detectable objects to be used in medical procedures, according to one embodiment.

FIG. 8 illustrates a process of manufacturing wirelessly detectable objects for use in medical procedures, such as pieces of gauze 14e each with a transponder device 20e attached thereto, according to one embodiment.

The process may begin with passing a roll of gauze through an attaching mechanism at 81 that attaches a plurality of transponder devices 20e to the roll of gauze. The attaching mechanism may attach the transponder devices 20e to the roll of gauze by heat sealing, such as RF welding, or sewing. In any case, the plurality of transponder devices 20e are attached to the roll of gauze before the roll of gauze is cut into discrete pieces of cut gauze by the gauze cutter at 82. After the roll of gauze is cut into discrete pieces of cut gauze 14e each having a respective transponder device 20e attached thereto, the pieces of cut gauze 14e may be folded and stacked into a pile or piles for further processing. With a transponder device 20e attached, each piece of cut gauze becomes a wirelessly detectable object. Additional processing may include packaging of the wirelessly detectable objects at 84 and/or testing the wirelessly detectable objects for operability at 85.

Attaching the transponder devices 20e to the roll of gauze before the roll of gauze is cut into discrete pieces of cut gauze 14e advantageously improves the efficiency associated with manufacturing of the wirelessly detectable objects, in terms of time and cost. Compared with the conventional process as shown in FIG. 7, the manufacturing process shown in FIG. 8 eliminates at least the unfolding and refolding of the pieces of cut gauze 14e. Furthermore, because the transponder devices 20e are attached to the roll of gauze, rather than being attached to discrete pieces of cut gauze 14e individually, the attachment may be done in a serial fashion that may advantageously speeds up the process and thus saves time and cost.

A batch of transponder devices 20e may be assembled and ready for attachment prior to the process shown in FIG. 8 begins. The transponder devices 20e may be provided as a batch of individual transponder pouches 31, as shown in FIG. 3A, or as a roll of transponder pouches 31, as shown in FIG. 3B, for example.

Figure 9:
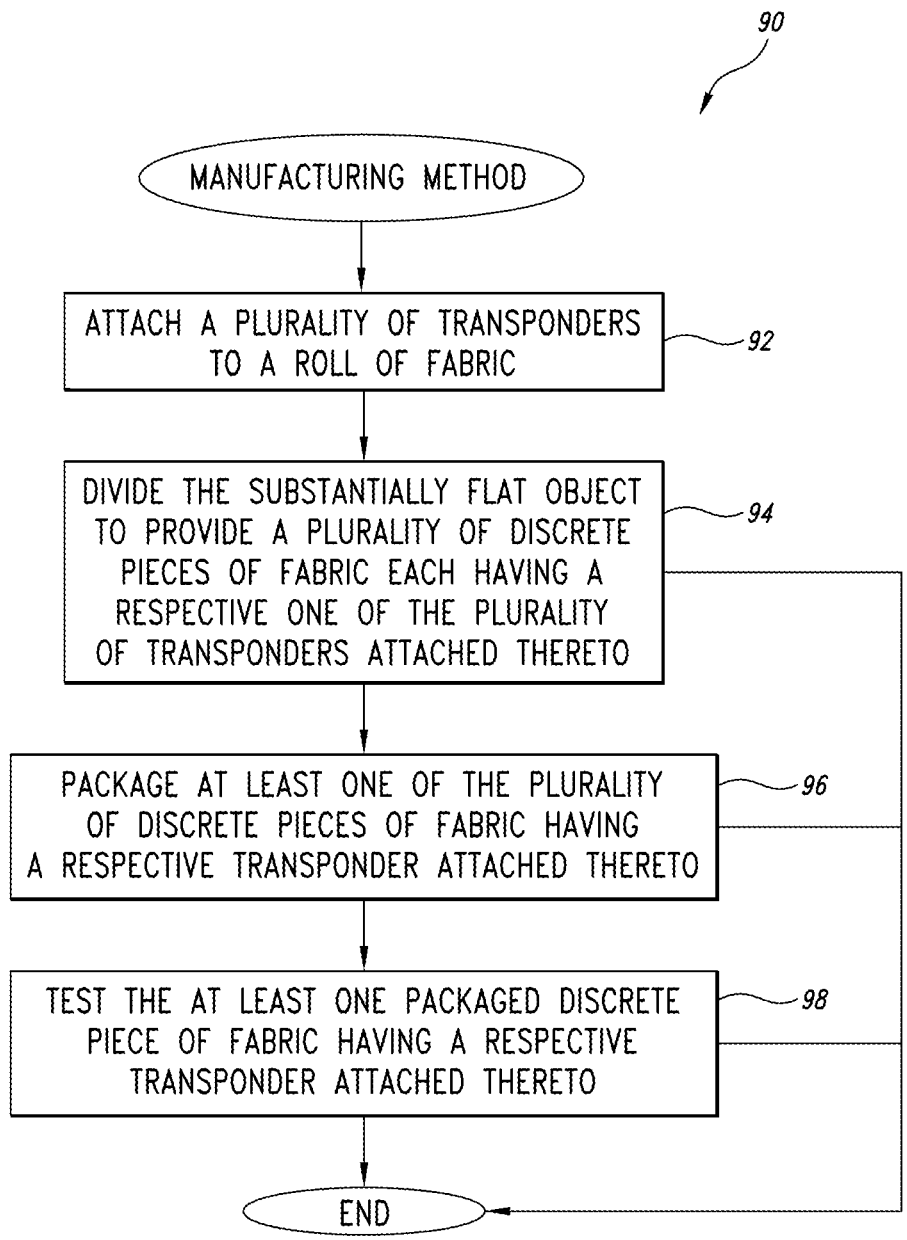
FIG. 9 is a flow diagram of a method for manufacturing a plurality of wirelessly detectable objects to be used in medical procedures, according to one embodiment.

FIG. 9 is a flow diagram of a method 90 for manufacturing a plurality of wirelessly detectable objects for use in medical procedures, according to one embodiment.

The method 90 begins at 92, where a plurality of transponders, such as transponder devices 20e, is attached to a roll of absorbent material. The roll of absorbent material may be a roll of gauze, for example. The roll of absorbent material is divided at 94 to provide a plurality of discrete pieces of absorbent material, each of which has a respective one of the plurality of transponders attached thereto. The manufacturing method 90 may end here as the discrete pieces of absorbent material, each having a respective transponder, can now be considered wirelessly detectable objects to be used in medical procedures. The method 90 may additionally include packaging one or more of the plurality of discrete pieces of absorbent material at 96. The method 90 may further include testing the packaged one or more discrete piece of absorbent material for operability at 98.

Figure 10:
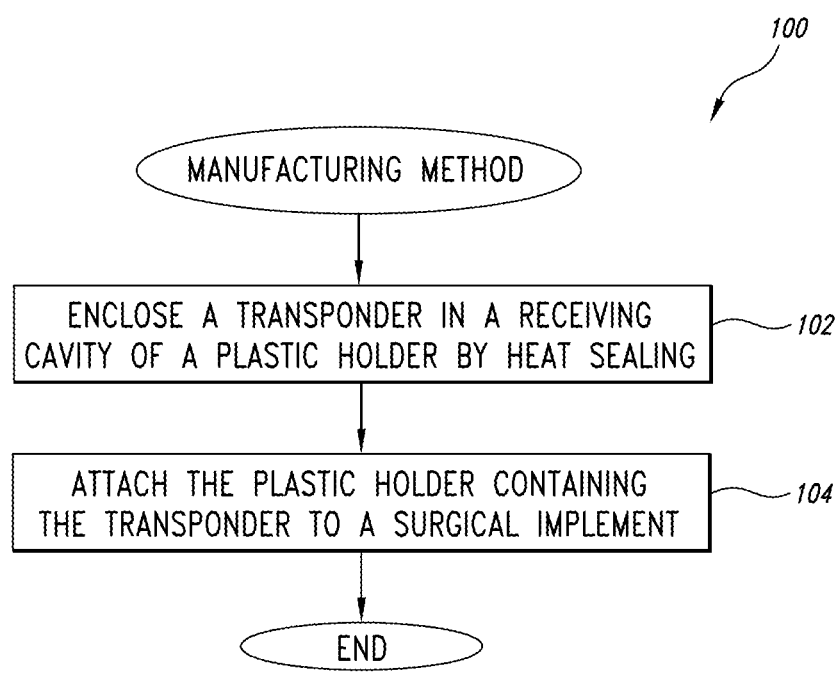
FIG. 10 is a flow diagram of a method for manufacturing a wirelessly detectable object to be used in medical procedures, according to one embodiment.

FIG. 10 is a flow diagram of a method 100 for manufacturing a wirelessly detectable object for use in medical procedures, according to one embodiment.

The method 100 begins with enclosing a transponder in a receiving cavity of a flexible holder by heat sealing at 102. RF welding may be the particular heat sealing method employed. Once the transponder is enclosed in the flexible holder, the flexible holder containing the transponder is attached to a surgical object at 104. The surgical object may be the surgical object 14e, such as a piece of gauze or lap sponge, for example.

The above description of illustrated embodiments, including what is described in the Abstract, is not intended to be exhaustive or to limit the various embodiments to the precise forms disclosed. Although specific embodiments of and examples are described herein for illustrative purposes, various equivalent modifications can be made without departing from the spirit and scope of the disclosure, as will be recognized by those skilled in the relevant art.

The teachings provided herein can be applied to other absorbent materials, other types of transponders, and other interrogation and detection systems. For instance, the transponder device may be used to mark objects anytime detection of the presence of marked objects is desirable in a confined area, not just during surgery. For example, it may be used to make sure marked objects are not left inside a machine (e.g., vehicle, copy machine) after maintenance is performed. In at least some embodiments, the transponder housing may be utilized to mark objects to determine the removal of a marked object from a confined area, such as a cover-all garment from a clean room of a semiconductor fabrication plant. In such an embodiment, an interrogation device, for example, may be placed proximate to a door of the confined area.

In addition, a transponder housing or cover may be manufactured and distributed for tagging objects without a transponder currently attached. Advantageously, the housing can then be used to place a transponder compatible with a particular detection and interrogation system at a subsequent time, including by the end-user.

The various embodiments described above can be combined to provide further embodiments. To the extent that they are not inconsistent with the specific teachings and definitions herein, all of the commonly assigned U.S. patents, U.S. patent application publications, U.S. patent applications referred to in this specification, including but not limited to U.S. patent application Ser. No. 12/606,686 filed Oct. 27, 2009; U.S. Provisional Patent Application Ser. No. 60/811,376 filed Jun. 6, 2006; U.S. Provisional Patent Application Ser. No. 60/892,208, filed Feb. 28, 2007; and U.S. provisional patent application Ser. No. 61/109,142 filed Oct. 28, 2008 are incorporated herein by reference, in their entirety. Aspects of the embodiments can be modified, if necessary, to employ systems, circuits and concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure.

I claim:

1. A wirelessly detectable object for use in medical procedures, comprising:
    a wireless transponder operable to wirelessly receive and transmit signals;
    a polyvinyl chloride (PVC) strip;
    a fabric laminate secured to the PVC strip to form a pouch, the wireless transponder enclosed within the pouch, and
    a piece of absorbent material, the PVC strip attached to the piece of absorbent material, wherein the PVC strip comprises a fabric impregnated with PVC.

2. The wirelessly detectable object of claim 1 wherein the PVC strip is radio-opaque.

3. The wirelessly detectable object of claim 2 wherein the PVC strip comprises a barium material.

4. The wirelessly detectable object of claim 1 wherein the piece of absorbent material is a one of a surgical sponge, a laparotomy (lap) sponge, or a piece of gauze.

5. The wirelessly detectable object of claim 1 wherein the PVC strip includes a sewing area, the sewing area spaced along the PVC strip from the wireless transponder such that the sewing area does not overlie or underlie the wireless transponder.

6. The wirelessly detectable object of claim 1, further comprising:
    a set of stitches which secure the PVC strip to the absorbent material.

7. A wirelessly detectable object for use in medical procedures, comprising:
    a polyvinyl chloride (PVC) strip that comprises a first piece of fabric impregnated with PVC;
    a second piece of fabric secured to the PVC strip to form a pouch therewith;
    a wireless transponder operable to wirelessly receive and transmit signals, the wireless transponder enclosed within the pouch; and
    a piece of absorbent gauze, the pouch containing the wireless transponder attached to the piece of absorbent gauze.

* * * * *